United States Patent [19]
Lane

[11] Patent Number: 4,993,404
[45] Date of Patent: Feb. 19, 1991

[54] FLUOROSCOPY SWITCHING DEVICE

[76] Inventor: Timothy G. Lane, 255 Madrid Ct., Merritt Island, Fla. 32953

[21] Appl. No.: 371,382

[22] Filed: Jun. 26, 1989

[51] Int. Cl.⁵ .......................... A61B 6/02; A61B 1/04; G21K 4/00; H04N 5/321
[52] U.S. Cl. ........................................ 128/4; 128/656; 250/358.1; 358/111; 358/181; 378/99; 378/114; 378/42
[58] Field of Search ..................... 128/4, 6, 653, 654, 128/656; 378/42, 99, 114, 116; 250/358.1, 359.1; 358/111, 181; 433/29-31

[56] References Cited

U.S. PATENT DOCUMENTS

| | | | |
|---|---|---|---|
| 3,448,606 | 6/1969 | Flaherty et al. | 128/660.04 |
| 3,622,785 | 11/1971 | Irwin | 378/99 |
| 3,675,020 | 7/1972 | Siedband et al. | 378/116 |
| 3,919,467 | 11/1975 | Peugeot | 378/99 |
| 4,037,107 | 7/1977 | Lutz et al. | 378/114 |
| 4,058,833 | 11/1977 | Meyer | 358/111 |
| 4,131,797 | 12/1978 | Franke | 250/322 |
| 4,349,750 | 7/1982 | Geurts | 358/181 |
| 4,358,855 | 11/1982 | Szasz et al. | 378/99 |
| 4,383,328 | 5/1983 | Kurihara et al. | 378/42 |
| 4,413,352 | 11/1983 | Nishio | 378/42 |
| 4,504,858 | 3/1985 | Franke | 358/111 |
| 4,569,334 | 2/1986 | Ohshiro | 128/6 |
| 4,658,413 | 4/1987 | Nishioka et al. | 378/99 |
| 4,677,477 | 6/1987 | Plut et al. | 378/99 |

FOREIGN PATENT DOCUMENTS

| | | | |
|---|---|---|---|
| 0056235 | 7/1982 | European Pat. Off. | 128/303.15 |
| 0088797 | 4/1988 | Japan | 378/99 |

Primary Examiner—Benjamin Layno
Attorney, Agent, or Firm—Jones, Askew & Lunsford

[57] ABSTRACT

An apparatus and method is disclosed for preventing accidental overradiation of a patient in surgical procedures involving both fluoroscopy and endoscopy. Video outputs from the fluoroscope and endoscope are connected to a switching device. The physician uses the switching device to select from between the endoscope video output and the fluoroscope video output for viewing on a video monitor. When the endoscope video output is selected for viewing, the switching device automatically deactivates the X-ray generator of the fluoroscope. When the switching device is actuated to select the fluoroscope video signal for viewing on the monitor, the switching device automatically reactivates the X-ray generator. In this manner, overradiation of the patient during periods when the fluoroscope is not being used is avoided.

12 Claims, 1 Drawing Sheet

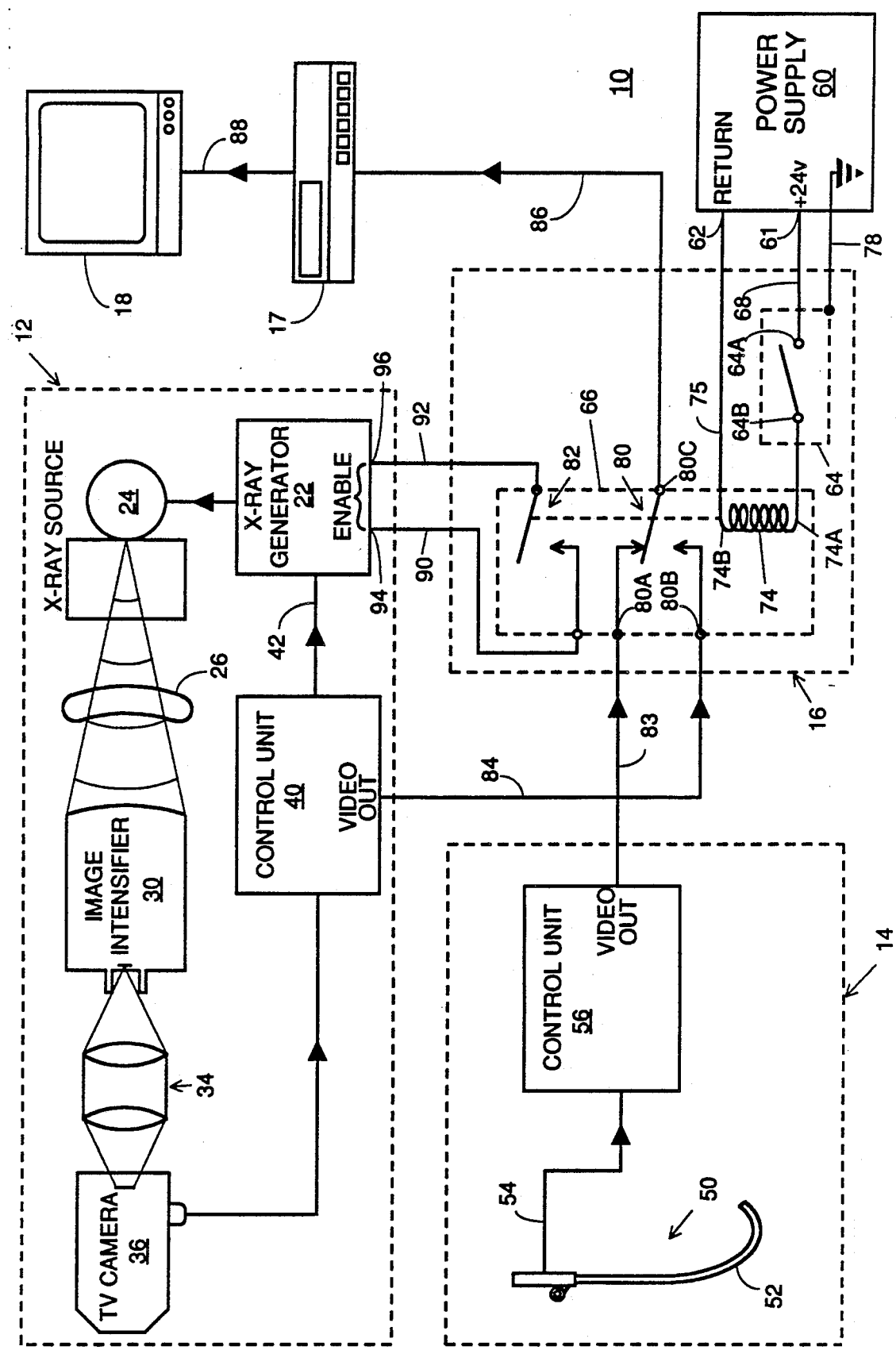

FLUOROSCOPY SWITCHING DEVICE

TECHNICAL FIELD

The present invention relates generally to apparatus for performing fluorscopy and relates more specifically to a switching device for preventing the accidental over-radiation of a patient and attending medical personnel during surgical procedures involving fluoroscopy and endoscopy.

BACKGROUND OF THE INVENTION

Endoscopes have long been widely used in medical procedures of directly visualizing the interior of a canal or body cavity. A recent improvement on the endoscope is the video endoscope, wherein fiber optics permit the endoscopic view to be displayed on a video monitor. Video endoscopy provides a number of advantages over traditional endoscopy, including permitting more than one person at a time to observe the endoscopic view, permitting the physician to assume a more comfortable viewing angle, and permitting a videotape record to be made of the endoscopic procedure.

Similarly, modern fluoroscopic technology presents advances over conventional radiography. In conventional radiography, X-rays are projected through a patient onto a photographic film which, when processed, will provide a fixed image of the patient's internal structure. In fluoroscopy, the X-ray sensitive photographic film is replaced by a fluorescent screen which, when subjected to X-radiation, produces a direct image of the object under investigation. Because the image on the fluorescent screen is usually so faint that it difficult to visualize with the unaided eye, the screen image is usually photographed with a sensitive video camera. The video signal is then processed to increase the brightness of the image, and the image is displayed on a video monitor for viewing by the physician. Fluoroscopy affords two primary advantages over conventional radiography: first the image produced is direct, so there is no need for photographic processing; and second, the image is viewed in "real time", rather than as a still photograph or series of still photographs, and can thus show movement.

Surgical modalities are well known wherein video endoscopy is used in conjunction with dye-injection studies under fluoroscopy at various times during the procedure. Examples of such procedures include endoscopic management of biliary tract obstruction and endoscopic sphincterotomy. In these procedures, the physician uses an endoscope to maneuver a catheter down the esophagus, through the stomach, and into position within either the bile duct or pancreatic duct. The endoscopic view is projected on a first video monitor. A quantity of radiographically opaque dye is then injected through the catheter retrograde into the selected duct. Subsequently, the duct is viewed fluoroscopically on a second video monitor, and the X-rays illuminate the dye to reveal obstructions in the biliary system. If the dye does not properly fill the duct, the catheter may have to be repositioned under endoscopic supervision to permit further infusion of dye. When further dye has been infused, the physician again views the duct fluoroscopically. After the procedure has been completed within the first duct, the physician uses the endoscope to reposition the catheter within the other of the bile or pancreatic duct, and the dye injection procedure is repeated. The physician then switches back to the fluoroscopic view to visualize the second duct. Depending upon the success of the initial dye injection into the second duct, the physician may again have to switch to the endoscope to reposition the catheter within the second duct, and then switch back to the fluoroscope to view the duct.

During steps when the physician is using the endoscope rather than the fluoroscope, fluoroscopy may inadvertently continue while the physician's attention is occupied with the endoscopic procedure. The patient and attending medical personnel are thus exposed unnecessarily to excessive dosages of X-rays during those periods when the physician is not actually viewing the fluoroscope. Thus, there is a need to provide a means for avoiding this accidental overexposure of the patient and attending medical personnel to X-rays during periods when the fluoroscope is not actually being used by the physician.

SUMMARY OF THE INVENTION

As will be seen, the present invention overcomes this and other problems associated with prior art modalities combining fluoroscopy and video endoscopy. Stated generally, the apparatus of the present invention comprises an apparatus for preventing the accidental over-radiation of a patient and attending medical personnel during surgical procedures involving endoscopy and fluoroscopy. A switching device has a video output for connection to a video monitor. Video outputs from a fluoroscope and an endoscope are both connected to the switching device. The switching device is operable to select the video output from the fluoroscope for output to the video monitor, or to deselect the fluoroscope view and select the video output from the endoscope for display on the video monitor. Concurrently with deselection of the fluoroscopic video output, the switching device disables the X-ray generator of the fluoroscope. Thus, by forcing the physician to select one or the other of the two views for display on a single monitor, the patient and attending medical personnel are not exposed to X-rays except during those periods when the physician is actually viewing the fluoroscope on the video monitor.

Thus, it is an object of the present invention to provide an improved apparatus for performing fluoroscopy.

It is a further object of the present invention to provide an apparatus for minimizing exposure of a patient and attending medical personnel to X-rays during procedures involving fluoroscopy and another video-assisted visualization technique.

It is another object of the present invention to provide a fluoroscopy apparatus wherein the X-ray generator is enabled only when the physician performing the procedure is actually viewing the fluoroscope.

Other objects, features, and advantages of the present invention will become apparent upon reading the following specification, when taken in conjunction with the drawings and the appended claims.

BRIEF DESCRIPTION OF THE DRAWING

The FIGURE is a schematic view of a switching device according to the present invention for use with fluoroscopic and endoscopic medical apparatus.

DETAILED DESCRIPTION OF THE DISCLOSED EMBODIMENT

Referring now to the drawing, the figure discloses an apparatus 10 for performing fluoroscopy in conjunction with endoscopy. The apparatus includes a fluoroscope 12, a video endoscope system 14, and a switching device 16 for directing a video output to an optional videocassette recorder 17 and to a video monitor 18.

The fluoroscope 12 is of conventional design well known to those skilled in the art and will be described only briefly. The fluoroscope 12 of the disclosed embodiment is the Philips Diagnost 92, though it will be appreciated that other fluoroscopes are easily adapted to the present invention. The fluoroscope 12 includes an X-ray generator 22, which is high-voltage power supply operatively connected by means of a line 23 to an X-ray source 24. The X-ray source 24 propagates X-rays through the patient 26 and onto an image intensifier 30. The image from the image intensifier 30 is projected through optics 34 onto the lens of a video camera 36, and the video output from the camera is sent by signal path 38 to a control unit 40. The control unit 40 samples the video signal from the camera 36 and automatically controls the dose rate of the X-ray generator 22 by sending a signal through a control line 42.

The video endoscope system 14 is also of conventional design and will thus be described only briefly. In the disclosed embodiment, the video endoscope system 14 is the Olympus CV-1, though it will again be appreciated that other brands and models of video endoscope systems will be easily adapted to the present invention. The system includes a video endoscope 50 comprising a flexible tubing 52 approximately 12 mm in diameter and 120 cm in length. The tubing 52 internally houses a fiber optic viewing tube, fiber optic light tubes for illuminating the field of view, and various guidewires for directing and manipulating the endoscope. An objective lens at the distal end of the fiber optic viewing tube projects an image of the field of view onto the lens of a miniature video camera mounted at the distal end of the endoscope 50. The video output from the endoscope 50 is then transmitted through a line 54 to a control unit 56 which processes image information from the endoscope.

Conventionally, the control unit 40 of the fluoroscope system 12 and the control unit 56 of the endoscope system 14 would send their respective video outputs to separate video monitors. However, according to the present invention, the video outputs from the fluoroscope and endoscope systems 12, 14 are instead both routed to the switching device 16. The switching device 16 operates to select one of the two video signals to provide a single video output to the videocassette recorder 17 and monitor 18, as will now be described.

The switching device 16 is connected to a low-voltage power supply 60. The power supply provides 24 volts DC between a pair of terminals 61, 62. In the disclosed embodiment, the 24 volt output is available at the X-ray table upon which the patient lies. The switching device 16 comprises a foot switch 64 and a relay 66. The foot switch 64 of the disclosed embodiment is a Gemswitch, catalog number GEM-36, manufactured by Linemaster Switch Corporation, though the invention is by no means limited to any particular footswitch. The foot switch 64 is of the "momentary contact" variety, whereby stepping on the foot switch closes the contacts and releasing the foot switch opens the contacts. One side 64A of the foot switch 64 is connected by a conductor 68 to the positive terminal 61 of the low voltage power supply 60. The other side 64B of the foot switch 64 is connected by a conductor 70 to one end 74A of a coil 74 of the relay 66. The other end 74B of the coil is connected by a conductor 75 to the return, or negative, terminal 62 of the low voltage power supply 60. As an additional safety precaution, the case of the foot switch 64 is connected by a grounding conductor 78 to a ground on the low voltage power supply 60. With the circuit arranged as described, actuating the foot switch 64 will close the circuit across the terminals 61, 62 of the power supply 60 and cause the relay 66 to be energized, and releasing the foot switch will open the circuit, de-energizing the relay.

The relay 66 of the disclosed embodiment of the switching device is manufactured by AMF Potter & Brumfield, part number KUP 11015, but it will be understood that this particular relay is disclosed only by way of example and is not critical to the invention. The relay 66 includes first and second switching elements 80 and 82. The video output of the endoscope 14 is connected via a signal path 83 to a normally closed contact 80A of the first switching element 80, and the video output of the fluoroscope 12 is connected via a signal path 84 to a normally open contact 80B of the first switching element. The pole 80C of the first switching element 80 is connected by a signal path 86 to the input of the videocassette recorder 17 and then, by signal path 88, to the monitor 18. In the disclosed embodiment, the signal paths 83, 84, 86, and 88 are shielded coaxial cables terminated in an appropriate connector, such as a BNC connector. When the relay 66 is not energized, the video output of the endoscope 14 will be connected via the switch element 80 to the videocassette recorder 17 and monitor 18. When the relay 66 is energized, the video output of the fluoroscope 12 will be connected via the switch element 80 to the videocassette recorder 17 and monitor 18.

The second switching element 82 of the relay 66 is a normally-open switch. The second switch element 82 is connected by a pair of signal paths 90, 92 to a pair of "enable" terminals 94, 96 on the X-ray generator 22 of the fluoroscope 12. When the relay 66 is not energized, the switch section 82 will present an open circuit between the "enable" terminals 94, 96 of the X-ray generator 22, and the X-ray generator will be disabled. However, when the relay 66 is energized, the switch section 82 is closed, thereby connecting the "enable" terminals 94, 96 and enabling the X-ray generator.

Thus, when the foot switch 64 is released to de-energize the relay 66, the video signal from the endoscope 14 is connected via the first switch element 80 to the videocassette recorder 17 and monitor 18, and the second switch element 82 is open to disable the X-ray generator 22. When the foot switch 64 is actuated to close the switch and energize the relay 66, the video signal from the fluoroscope 12 is connected via the first switch element 80 to the videocassette recorder 17 and monitor 18, and the second switch element 82 is closed to enable the X-ray generator 22. It will thus be appreciated that the switching device 16 serves a dual purpose: it selects from between the video signals from the fluoroscope 12 and endoscope 14 for output to the monitor 18; and, responsive to deselection of the video signal from the fluoroscope, it disables the X-ray generator 22 of the fluoroscope 12. As a consequence, the X-ray generator of the fluoroscope is enabled only when the physician steps on the foot switch 64 to select the video signal from the fluoroscope for display on the video monitor 18.

It is not required that the relay 66 operate off of 24 volts. Rather, a 24 volt relay was selected because of the availability of a 24 volt output at the X-ray table of the fluoroscope and because of the desire to use a low voltage for the switching relay from a safety perspective. It will also be appreciated that a reverse-biased diode or a varistor (not shown) may be connected across the coil 74 in a conventional manner to reduce sparking in the foot switch 64 when the switch is released.

The use of the fluoroscopic switching device 10 will now be described with respect to a diagnostic procedure known as an endoscopic retrograde cholangiopancreatography ("ERCP"). The initial phase of this procedure is carried out under endoscopic supervision. To activate the video switching device 16 to display the endoscopic view on the monitor 18, the foot switch 64 is released to de-energize the relay 66. As a consequence of de-energizing the relay, the first switching element 80 is closed to connect the video signal from the endoscope to the monitor 18 and videocassette recorder 17. As a further consequence of de-energizing the relay 66, the second switching element 82 is open, thereby interrupting the circuit across the "enable" terminals 94, 96 at the X-ray generator 22 and disabling the X-ray generator. Thus, while the endoscopic view is being displayed on the monitor 18, no X-radiation is being emitted.

With the endoscopic view thus displayed on the monitor, the physician passes the distal or viewing tip of the endoscope down the esophagus of the patient, through the stomach, and into the duodenum. Monitoring the endoscopic video image on the monitor, the physician locates the ampulla of Vater, the opening of the bile and pancreatic ducts. A polyethylene catheter is then inserted under endoscopic guidance into the opening of the bile duct. Radiographically opaque dye is injected retrograde to fill the biliary system, including the gall bladder (if present) and bile ducts and up into the liver.

The physician then switches to the fluoroscopic view. To display the fluoroscopic view on the video monitor, the physician activates the foot switch 64, thereby closing the switch and energizing the relay 66. Energizing the relay 66 closes the first and second switching elements 80, 82. Closing the second switching element 82 completes the circuit across the "enable" terminals 94, 96 and actuates the X-ray generator 22. X-rays are then propagated through the patient 26 and onto the image intensifier 30, and the resulting image is projected onto the lens of the video camera 36. The video signal is transmitted to the control unit 40 of the fluoroscope, which samples the signal and automatically controls the dose rate of the X-ray generator 22 by sending a signal via signal path 42. The video output from the fluoroscope is then transmitted through the coaxial cables 84 and across the closed first switching element 80 to the monitor 18.

The physician uses the fluoroscopic view to visualize the biliary system. If the dye has not satisfactorily filled the biliary system, the physician may switch back to the endoscopic view to reposition the catheter to infuse an additional quantity of dye into the biliary system. When the physician releases the foot switch 64, the relay is again de-energized, opening the first switching element 80 to deselect the fluoroscope view and causing the endoscope view to be displayed on the video monitor. Concurrently, de-energizing the relay 66 opens the second switching element 82, opening the circuit across the "enable" terminals 94, 96 and disabling the X-ray generator 22. The risk of accidental exposure of the patient and attending medical personnel to X-rays while the physician is employing the endoscope is thereby eliminated.

When the catheter has been repositioned under endoscopic guidance and additional radiographically opaque dye has been injected into the biliary system, the physician actuates the switching device to switch back to fluoroscopy. Upon reselection of the fluoroscope, the switching device re-enables the X-ray generator. The physician again visualizes the biliary system on the video monitor to verify proper dye distribution throughout the biliary system.

When the biliary system has been properly filled with radiographically opaque dye, dye must be infused into the pancreatic duct. The physician releases the foot switch 64 to deselect the fluoroscope view and to display the video image from the endoscope on the video monitor 18. As the fluoroscope view is deselected, the second switching element 82 is again opened, interrupting the circuit across the "enable" terminals 94, 96 and disabling the X-ray generator 22. The catheter is then manipulated under endoscopic guidance to position the end of the catheter within the pancreatic duct. A quantity of radiographically opaque dye is then infused into the pancreatic duct, and the physician actuates the switching device to display the fluoroscopic view on the video monitor. Stepping on the foot switch 64 to actuate the switching device 16 to select the fluoroscopic view closes the second switching element 82 to enable the X-ray generator 22, thereby illuminating the dye in the pancreatic duct. If proper dye distribution throughout the pancreatic system is not achieved, the physician may have to switch back to the endoscope to reposition the catheter to infuse an additional quantity of dye. Each time the physician selects the endoscopic view, thereby deselecting the fluoroscopic view, the X-ray generator 22 is disabled to prevent exposure of the patient and attending medical personnel while the physician is viewing the endoscope.

When the biliary and pancreatic systems have been properly infused with radiographically opaque dye, the physician can use the fluoroscopic view to look for strictures or stenosis, dilation, or stones in the biliary system. In the pancreas, the physician looks for abnormalities or strictures. A ragged stricture in the pancreas may indicate cancer. If desired, a "hard copy" photograph of the fluoroscope may be taken directly from the image intensifier 30 or from the video monitor 18. Also, a record of the entire procedure may be made using the videocassette recorder 17. Since the video signal input into the videocassette recorder is the same signal being input into the video monitor, the resulting videocassette tape will show the serial sequences of endoscopy and fluoroscopy, thereby providing not only an accurate record of the procedure but also a valuable teaching tool.

While the use of the switching device 16 has been illustrated with respect to a diagnostic procedure, it will be appreciated that the invention is equally well suited for therapeutic applications involving fluoroscopy and video endoscopy. For example, the physician may maneuver a radiographically opaque balloon catheter into an obstructed duct under endoscopic guidance and then switch to fluoroscope to inflate the balloon and monitor its effects. As the physician uses the foot switch 64 to select from between endoscopic and fluoroscopic views, the switching device 16 enables or disables the X-ray generator 22 of the fluoroscope 12 to prevent irradiation of the patient and attending medical personnel during those periods when the physician has deselected the fluoroscopic view on the monitor.

While the present invention has been disclosed with respect to a switching device for selecting from between a fluoroscopic view and an endoscopic view, it will be appreciated that the switching device may also be employed in conjunction with a fluoroscope and any other video-assisted visualization apparatus, with the same benefits of reducing exposure to X-ray during those periods when the physician has deselected the fluoroscope. Also, it will be understood that the switching device of the present invention may be adapted to select from among more than two video inputs, with the X-ray generator being disabled in response to selection of any video input other than the fluoroscope.

In the disclosed embodiment, energizing the single relay 66 causes both of the switching elements 80, 82 to be actuated, concurrently selecting from between the video inputs and enabling or disabling of the X-ray generator, as appropriate. While the disclosed embodiment depicts both the selection from between the video inputs and the enabling or disabling of the X-ray generator as being actuated in response to the same mechanism, i.e. the relay 66, it will be appreciated that the actions need not necessarily be performed in direct response to the same mechanism. For example, actuation of the foot switch may directly precipitate only one of the two actions, with the other of the actions being initiated responsive to performance of the first action. Further, while the relay 66 switches both switching elements 80, 82 simultaneously, it is not critical to the invention that both switching actions take place simultaneously. Thus, the present invention contemplates an arrangement which produces a slight delay between the two actions, and references herein to the two actions taking place "concurrently" are to be understood to mean that the actions occur at substantially the same time.

Finally, it will be understood that the preferred embodiment has been disclosed by way of example, and that other modifications may occur to those skilled in the art without departing from the scope and spirit of the appended claims.

What is claimed is:

1. An apparatus for performing a surgical procedure involving endoscopy and fluoroscopy, comprising:
    a switching device having a video output for connection to a video monitor;
    an endoscope having a video output connected to said switching device;
    a fluoroscope having an X-ray generator, said fluoroscope further having video output connected to said switch device;
    said switching device being operable to select from between said video output from said endoscope and said video output from said fluoroscope for output to said video monitor; and
    means operative concurrently with selection by said switching device of said video output from said endoscope for deactivating said X-ray generator of said fluroscope.

2. The apparatus of claim 1, further comprising means operative concurrently with selection by said switching device of said video output from said fluoroscope for activating said X-ray generator.

3. The apparatus of claim 1, wherein said switching device comprises a foot-operated switching device.

4. An apparatus for performing a surgical procedure involving endoscopy and fluoroscopy, comprising:
    a switching device having a video output for connection to a video monitor;
    an endoscope having a video output connected to said switching device;
    a fluoroscope having an X-ray generator, said fluoroscope further having a video output connected to said switching device;
    said switching device being operable to select from between said video output from said endoscope and said video output from said fluoroscope for output to said video monitor; and
    control means operatively associated with said X-ray generator and said switching device and operative to select from between a first mode in which said fluoroscope video output is selected by said switching device and said X-ray generator is enabled, and a second mode in which said fluoroscope video output is not selected by said switching device and said X-ray generator is disabled.

5. The apparatus of claim 4, wherein said switching device comprises a foot-operated switching device.

6. A switching device for use with an endoscope and a fluoroscope having an X-ray generator, comprising:
    a video output for connection to a video monitor;
    a pair of video inputs for receiving video signals from said endoscope and said fluoroscope;
    means for selecting from between said pair of video inputs for output to said video monitor; and
    means operative concurrently with selection of said video output from said endoscope for output to said video monitor for deactivating said X-ray generator of said fluoroscope.

7. The apparatus of claim 6, further comprising means responsive to selection of said video output from said fluoroscope for activating said X-ray generator.

8. The apparatus of claim 6, wherein said switching device comprises a foot-operated switching device.

9. A switching device for use with a pair of video devices generating video signals, comprising:
    a video output for connection to a video monitor;
    a pair of video inputs for receiving video signals from said pair of video devices;
    means for selecting from between said pair of video inputs for output to said video monitor; and
    means responsive to selection of the video input from one of said devices for disabling the other of said devices.

10. The switching device of claim 9, further comprising means responsive to the selection of the video input from said other of said devices for enabling said other of said devices.

11. A method for preventing the accidental over-radiation of a patient during a surgical procedure involving endoscopy and fluoroscopy, comprising the steps of:
    selecting from between a video signal from an endoscope and a video signal from a fluoroscope having an X-ray generator for viewing on a single video monitor; and
    concurrently with selection of said video signal from said endoscope for viewing on said monitor, disabling said X-ray generator of said fluoroscope.

12. The method of claim 11, comprising the further step of enabling said X-ray generator of said fluoroscope responsive to selection of said video signal from said fluoroscope.

* * * * *